Figure 1:
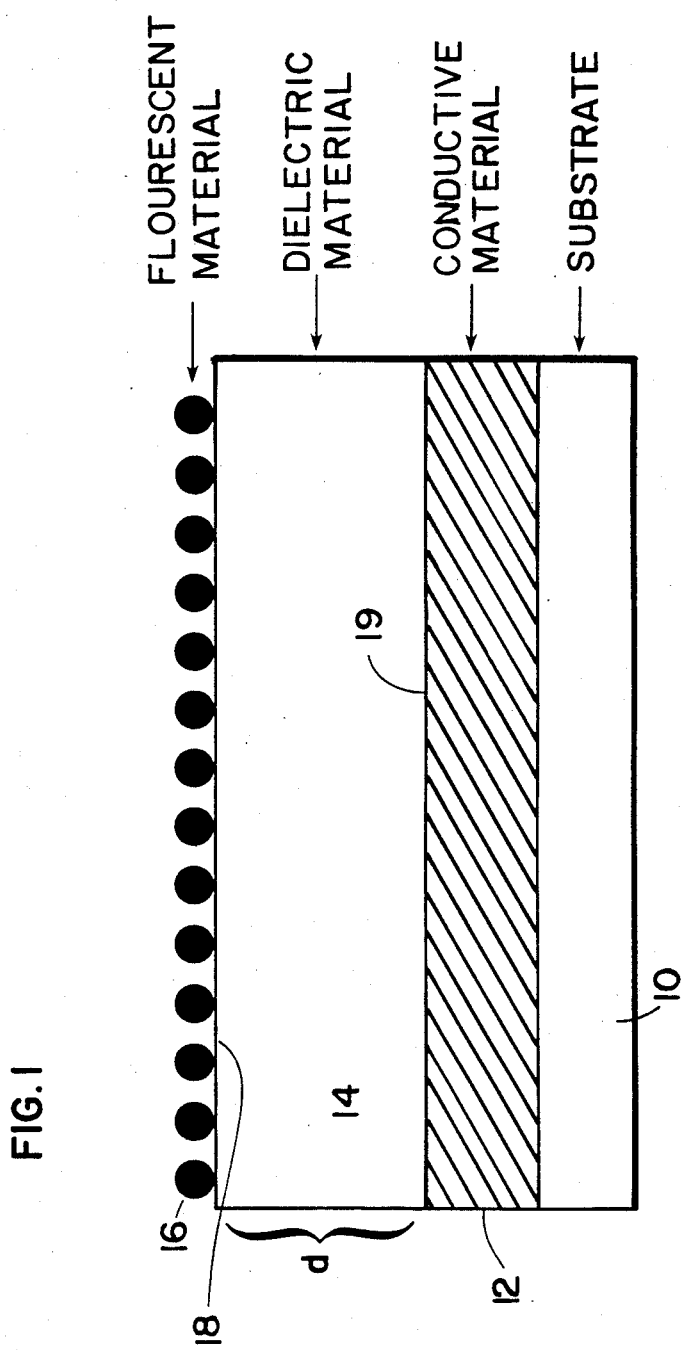

United States Patent [19]

Holland et al.

[11] Patent Number: 4,649,280

[45] Date of Patent: Mar. 10, 1987

[54] METHOD AND SYSTEM FOR THE ENHANCEMENT OF FLUORESCENCE

[75] Inventors: William R. Holland; Dennis G. Hall, both of Rochester, N.Y.

[73] Assignee: The University of Rochester, Rochester, N.Y.

[21] Appl. No.: 732,773

[22] Filed: May 10, 1985

[51] Int. Cl.[4] .............................................. G01J 1/58
[52] U.S. Cl. .............................. 250/483.1; 250/487.1; 250/368
[58] Field of Search ............... 250/483.1, 484.1, 487.1, 250/488.1, 368

[56] References Cited

U.S. PATENT DOCUMENTS 3,992,631 11/1976 Harte ..................................... 250/365
4,262,206 4/1981 Viehman ............................. 250/368
4,371,897 2/1983 Kramer ............................... 250/368

OTHER PUBLICATIONS

Glass et al, "Interact. of Metal Particles with Absorb. Dye", *Optics Letters*, vol. 5, No. 9, Sep. 1980, p. 368.
Holland et al, "Surface-Plasman Dispersion . . . ", *Physical Review B*, vol. 27, No. 12, Jun.-83, p. 7766.
Drexhage, K. "Interaction of Height with . . . Dye Layers", Progress in Optics, Ed. E. Wolf, vol. XII, 1974, p. 191.

*Primary Examiner*—Carolyn E. Fields
*Assistant Examiner*—Richard Hanig
*Attorney, Agent, or Firm*—Martin LuKacher

[57] ABSTRACT

Fluorescence enhancement is obtained using an optical waveguide consisting essentially of films of fluorescent molecules and of conductive material separated by a dielectric layer. The enhancement is believed to be due to the near field interaction between the molecules of the fluorescent material and the waveguide modal fields. No special couplers (prisms or gratings) are needed between the fluorescent material and the waveguide. The enhancement factor is in excess of two orders of magnitude over fluorescence from the material without the use of the waveguide.

23 Claims, 3 Drawing Figures

METHOD AND SYSTEM FOR THE ENHANCEMENT OF FLUORESCENCE

DESCRIPTION

The present invention relates to methods and systems for the enhancement of fluorescence, and particularly to fluorometric systems and methods whereby the presence, concentration or absence of substances may be determined.

The invention is especially suitable for use in fluorescent assay methods and apparatus wherein substances to be assayed are coated onto a substrate in fluorescent form. The fluorescence is detected to provide a signal from which the presence and nature of the substance may be determined. Reference may be had to U.S. Pat. No. 3,992,631 issued Nov. 16, 1976, further information respecting fluorescent assay methods and apparatus of the types which have heretofore been proposed.

It is desirable in fluorescent assay techniques that the intensity of the fluorescence be significant so as to enable the detection thereof by photodetectors to provide electrical signals much larger than the noise. Otherwise the presence and concentration of the substances of interest cannot be quantitatively determined with acceptable accuracy.

In conventional fluorescent assay systems the material to be assayed is labeled with fluorescent material and coated on a glass slide. The coated slide is then exposed to excitation light and the emitted fluorescence is photodetected to obtain the signal which is analyzed. Utilizing the method and system provided by the invention can give rise to an enhancement factor over the conventional system in excess of two orders of magnitude (over 100 times enhancement).

Enhancement of fluorescence has been reported utilizing layers of fluorescent material deposited on silver island films. See A.M. Glass et al., Optics Letters, Vol. 5, No. 9, pp. 368-370 (September 1980). An enhancement of the fluorescence of about one order of magnitude is reported by Glass et al. Glass et al. and other investigators have ascribed the enhancement to molecule-surface interaction processes. See A.M. Glass et al., Phys. Rev. B 24, 4906 (1981); A. Wokaun et al., Phys. Rev. B 24, 849 (1981); D. A. Weitz et al., Opt. Lett. 7, 89 (1982); D.A. Weitz et al., J. Chem. Phys. 78(9), 5324 (1983); W. R. Holland, Phys. Rev. B 27(12) 7765 (1983); and W. R. Holland et al., Phys. Rev. Lett. 52(12), 1041 (1984).

In accordance with the present invention, the modes of an optical waveguide are used to generate a strong field in the vinicity of a film of fluorescent material, and particularly from the layer of molecules of the material which defines a wall of the optical waveguide. The remainder of the waveguide is defined by a layer of dielectric material having a film of conductive (preferably also reflective) material on the surface of the dielectric layer opposite that on which the layer of fluorescent molecules is disposed. The excitation radiation which is incident on the fluorescent material is self-coupled to the waveguide to support the propagation of the modes which generate the strong field. No external means such as prisms or gratings are required to couple the incident excitation into the modes of the optical waveguide. The system is simple in configuration and provides fluorescence that is enhanced in the range of two orders of magnitude over that from the same quantity of fluorescent material deposited on a glass substrate (typically a microscope slide), as would be the case if conventional fluorescent assay techniques were followed.

The fluorescence enhancement is believed to be attributable to the coupling between the molecules of the fluorescent material and the propagating modes of the system. The operation of the waveguide mode enhancement of molecular fluorescence provided by the invention may be appreciated better by analogy to an antenna having an emitting dipole closely coupled to a directive structure which has gain at the wavelengths over which coupling occurs. The molecular overlayer provided by the molecules of fluorescent material is critical to the enhancement and gain from the system. In the absence of the molecular overlayer, a plane-wave incident on a substrate from air has a parallel (to the surface of the substrate) wave-vector component that is too small to permit excitation of guided modes in a waveguide structure. Because the near-field of a molecule contains a large distribution of parallel (to the surface) wave-vector component values, the presence of the layer of molecules in the waveguide structure effects the coupling between the incident, fluorescent exciting light and the waveguide modes because of the spatial overlap between the dipole field from the molecule and the modal fields in the waveguide structure. The net effect of the coupling is an enhanced molecular absorption rate due to the large local (to each molecule) fields produced by the modes at the wavelength of the incident light, and an enhanced radiative effect due to the coupling with the modes at the emission wavelength (the wavelength of the fluorescence). It should be understood that the foregoing theoretical discussion and the analogy to an antenna is theoretical and is given in order to facilitate an understanding of the invention and is not intended to limit the invention to any mode of operation, theoretical or otherwise.

Accordingly, the principal object of the invention is to provide an improved method and system for the enhancement of fluorescence.

More specifically, it is an object of the present invention to provide an improved method and system for obtaining enhanced fluorescence from the molecules of fluorescent material deposited on and defining the surface of an optical waveguide structure.

It is a still further object of the present invention to provide improved methods and systems whereby fluorescent assays may be carried out.

Figure 2:
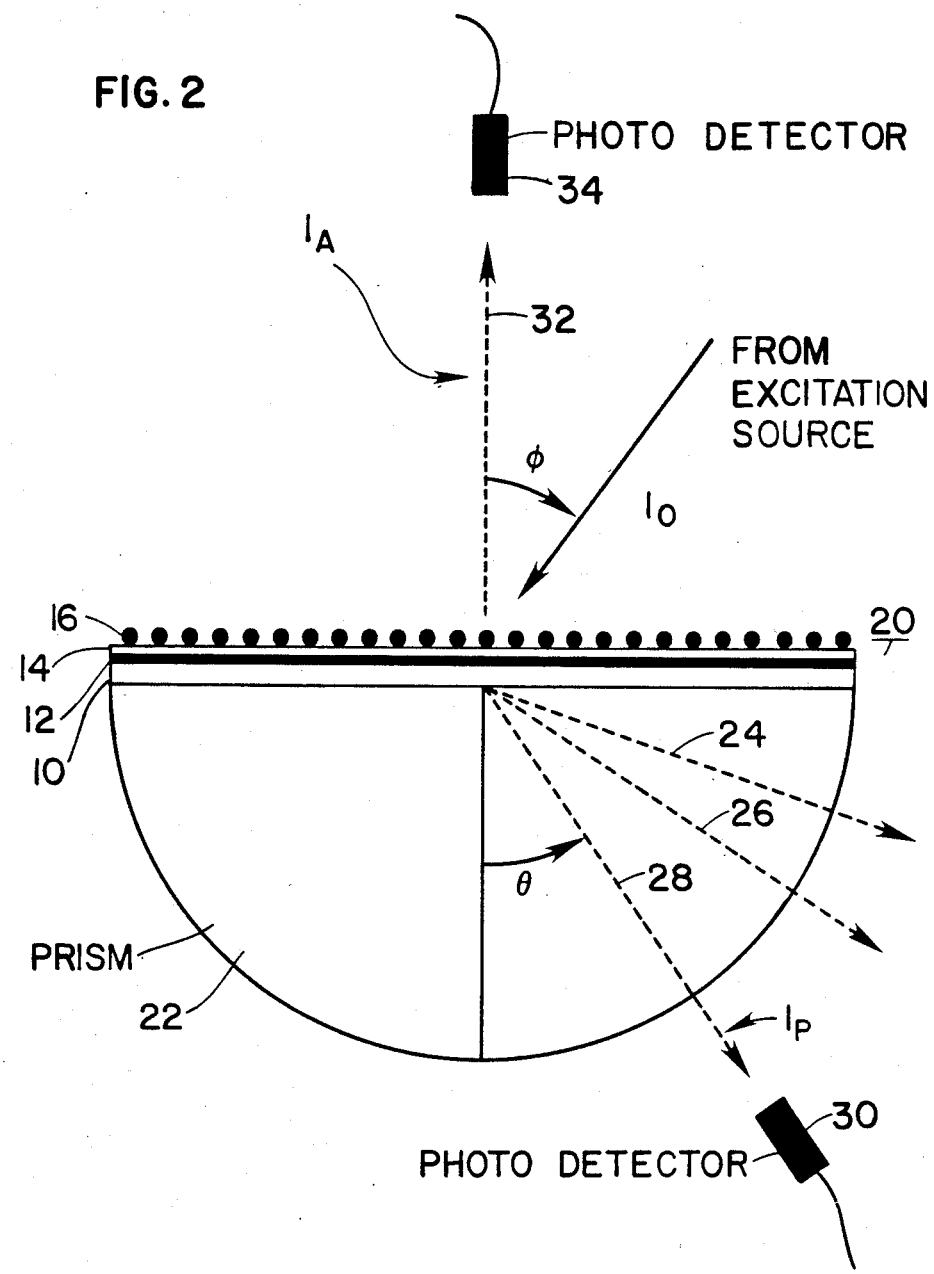
Figure 3:
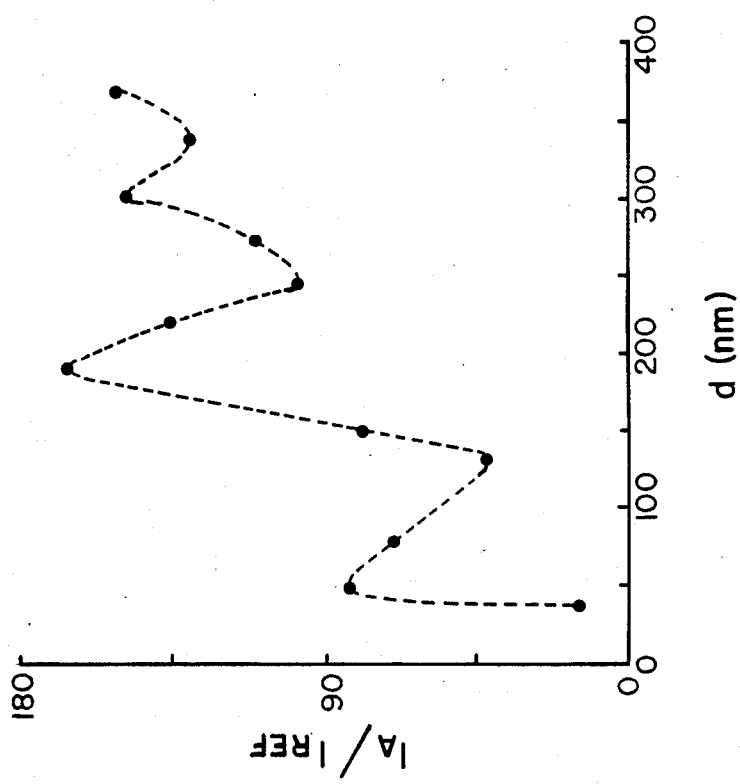

The foregoing objects, features and advantages of the invention, as well as a presently preferred embodiment thereof, and the best mode now known for carrying out the invention, will become more apparent from a reading of the following description in connection with the accompanying drawings in which:

FIG. 1 is a schematic diagram of the crosssection of a system for enhancing fluorescence in accordance with the invention;

FIG. 2 is a schematic diagram illustrating the operation of the system and the method for enhancing the detection of fluorescence in accordance with the invention; and FIG. 3 is a plot illustrating the enhanced fluorescence as a function of the thickness of the layer of dielectric material, d, in the structure illustrated in FIGS. 1 and 2 in terms of the ratio of the intensity of the fluorescence, $I_A$ from the system in accordance with the invention to $I_{REF}$ which is the intensity of the fluorescence from a reference sample wherein the fluorescent material is directly deposited on an uncoated glass slide.

Referring first to FIG. 1, there is shown, schematically, a diagram of a three layer structure which provides the fluorescence enhancement system in accordance with a presently preferred embodiment of the invention. A glass substrate 10, which may be a rectangular glass slide, is coated with a film 12 of conductive, reflective material. Vacuum deposition techniques of the type normally used in the fabrication of optical devices may be used. Preferably the film covers the entire slide and may have a thickness which enables the film 12 to be partially transparent, for example, partially transmissive of 20% of the light which is incident normal to the surface thereof. The thickness of this film 12 is suitably 50 nanometers (nm) when the film material is the metal Ag. Other metals may need other thicknesses.

A layer 14 of thickness, d, of a transparent dielectric material is deposited upon the conductive, reflective film 12 and extends over the entire area of the slide 10. Suitably, this layer is of Lithium Flouride (LiF), and other dielectrics are usable as well. This thickness, d, of the layer 14 is critical and depends upon the wavelength of the exciting, incident radiation and the emissions (fluorescence) wavelength, as will be apparent from FIG. 3. In an exemplary embodiment, the depositions of the film 12 and the layer 14 were made by thermoevaporation in a cryogenically pumped system at pressures in the $10^{-8}$ Torr range. Film thicknesses may be measured using a quartz-crystal film-thickness monitor.

A film of fluorescent material 16 is deposited over the dielectric layer 14. It is illustrated as the row of solid black spheres to schematically show the molecular layer at the interface 18 between the film of fluorescent material 16 and the layer of dielectric material 14. The fluorescent material may be organic material, such as Rhodamine B, or any other materials, the molecules (organic or inorganic) of which are labelled with a fluorescent component. The fluorescent component may be bound to the molecule of interest in accordance with techniques used in fluorescent assays. The thickness of the layer 16 is desirably of the order of single molecules in thickness. The thickness is not especially critical. It is important, however, that the layer 16 not be so thick that the incident, exciting light does not reach molecules which are close to the interface 18. The interface 18 and the interface 19 between the layer 14 and conductive film 12 are desirably in parallel planes.

By way of example, the fluorescent material layer 16 may be applied after the device coated with the conductive layer 12 and dielectric layer 14 is removed from the vacuum system. The device is immediately placed in a second vacuum system equipped with a resistively heated source containing solid organic material, for example, the organic dye Rhodamine B. Extremely slow heating of the dye (at a pressure of approximately $2$ times $10^{-6}$ Torr) to a temperature near its melting point of approximately 275° C. causes the organic dye to vaporize to form a thin layer of dye on the interface 18. In this example the dye evaporation is stopped when the quartz-crystal film thickness monitor registers a thickness of 30 Angstroms, approximately. This is an approximation since it is based on the assumption that the dye has a density of one gram per cubic centimeter. Other techniques may be used to provide the film of fluorescent material 16, for example, by dipping to provide well-ordered layers in accordance with the Langmuir-Blodgett technique or by spin coating of the material in liquid form, suitably dissolved in a solvent, and placed on the interface 18.

The fluorescent material film 16, the dielectric layer 14 and the layer of reflective conductive material define an optical waveguide which supports a plurality of propagation modes including the $TE_0$ and the $TM_1$ modes.

The presence of these modes and the existence of waveguide propagation is demonstrated in the apparatus shown in FIG. 2 where the device 20 is similar to the device shown in FIG. 1 and has the fluorescent material film 16, the dielectric layer 14, the conductive layer 12 and the substrate 10. A prism 22 which is index-matched to the substrate 10 allows the projection of fluorescence indicated by the rays 24, 26 and 28 at angles, $\theta$, to a photodiode detector. The rays 24, 26, and 28 designate light emitted by the waveguide modes at the fluorescence wavelength. The intensity of this radiation is shown as $I_P$ and is detected by a photodetector 30 which may suitably be a photomultiplier followed by a photon-counting electronics system. A slit and filter which blocks the excitation wavelength is suitably placed in the path of the rays 24 to 28 ahead of the photodetector 30.

The incident, exciting wavelength may be a light beam from an excitation source, suitably a laser, however, an incandescent light-source is usable. In the case of Rhodamine B the excitation wavelength may be from an Argon-Ion laser at a wavelength of 514.5 nm. The beam may be of low power (for example less than 1/10th milliwatt). The fluorescence wavelength is 540 nm. The incident beam is indicated as arriving at an angle of incidence, $\phi$, and the intensity of the incident radiation is indicated as $I_0$. The fluorescence is indicated by the ray 32 and its intensity is indicated as $I_A$. A photodetector 34 detects the fluorescence. A monochrometer may be used to select the fluorescence wavelength. The photodetector may also be a photomultiplier followed by a photon-counting electronic system.

The enhancement is shown in FIG. 3. FIG. 3 is for the exemplary case where the excitation beam is at an angle of incidence, $\phi$, of approximately 15° and the fluorescence is observed along the normal as shown in FIG. 2. The vertical axis of the plot of FIG. 3 is labeled in units of enhancement quantity, $I_A/I_{REF}$, where $I_{REF}$ is the fluorescence signal obtained from a similar dye layer deposited on an uncoated microscope slide.

The enhancement of the fluorescence is attributed to the coupling between the dye molecules at or close to the interface 18 and the propagating modes of the waveguide structure. It will be observed that the enhancement is in excess of two orders of magnitude where the dielectric layer is approximately 180 nanometers, for the Rhodamine B fluorescent material used in the above example. Of course the thickness d will depend upon the excitation and emission wavelengths and is selected as a compromise so that modes of propagation at both the incident and the emission wavelengths will be supported by the waveguide. The thickness of the conductive film 10 is not critical when measurements such as that of $I_P$ are not needed. The propagating modes of optical radiation are best supported when the conductive layer is substantially fully reflective of the exciting radiation and also of the fluorescence (the emitted radiation from the fluorescent material film 16). Other variations and modifications within the scope of the invention will undoubtedly suggest themselves to those skilled in the art. Accordingly, the foregoing description should be taken as illustrative and not in a limiting sense.

I claim:

1. The method of enhancing the detection of fluorescence of a material which comprises the steps of providing with a film of said material a waveguide which supports propagation modes for optical radiation at the wavelength of the fluorescence from said material, exciting fluorescence from said film/substrate waveguide and detecting said fluorescence from said film/substrate waveguide, wherein said waveguide is defined by a dielectric layer of predetermined thickness which maximizes the intensity of said fluoroescence, and films of said fluorescent material and conductive mateiral on opposite surfaces of said layer.

2. The method according to claim 1 wherein said waveguide providing step comprises depositing on a substrate a plurality of films including a film of said fluorescent material, a layer of dielectric material, and a film of conductive material.

3. The method according to claim 2 wherein said dielectric material layer is deposited with a pre-determined thickness to separate said films by a distance selected to maximize the enhancement of the intensity of said emitted fluorescence.

4. The method according to claim 3 wherein said depositing step is carried out in the sequence whereby said conductive film is deposited on said substrate, said dielectric material layer is deposited over said conductive film, and said film of said fluorescent material is deposited over both said layer and said conductive film.

5. The method according to claim 4 wherein said depositing step is carried out such that the interfaces between said layers and said films are in parallel planes.

6. The method according to claim 1 wherein said film of said fluorescent material is deposited in a manner to provide a thin film of said fluorescent material of thickness of the order of the length of single molecules thereof.

7. The method according to claim 4 wherein said conductive film and layer are deposited by vacuum deposition, and said film of fluorescent material is deposited by vacuum deposition to provide a layer of thickness of the order of single molecules of said fluorescent material.

8. The method according to claim 3 wherein said substrate is glass, said dielectric layer is a transparent dielectric material, and said fluorescent material contains organic material.

9. The method according to claim 8 wherein said dielectric material is LiF.

10. The method according to claim 8 wherein said organic material is an organic fluorescent dye.

11. The method acording to claim 2 wherein said conductive material is reflective at the wavelength at which said fluorescence is excited and emitted.

12. The method according to claim 1 wherein said the detecting step is carried out by detecting said fluorescence intermediate the ends of said wave guide.

13. A system for providing enhanced fluorescence from a fluorescent material which comprises a waveguide which supports modes of propagation for fluorescence from said material, said material being disposed with the molecular electromagnetic fields thereof in closely coupled relationship to the electromagnetic fields corresponding to said modes of propagation of said waveguide, wherein said waveguide is defined by a dielectric layer of predetermined thickness which maximizes the intensity of said fluorescence, and films of said fluorescent material and conductive material on opposite surface said layer.

14. The system according to claim 13 wherein said film and layer are disposed on a substrate.

15. The system according to claim 14 wherein said conductive film is disposed on said substrate and said layer and fluorescent material films are disposed successively over said conductive film.

16. The system according to claim 14 wherein said films, and layer are rectilinear in shape.

17. The system according to claim 13 wherein said interfaces between said layer and said films are in parallel planes.

18. The system according to claim 11 wherein the thickness of said fluorescent film is of the order of the length of single molecules of said fluorescent material.

19. The system according to claim 14 wherein said substrate is glass, said dielectric layer is a transparent dielectric, and said fluorescent material contains organic material.

20. The system according to claim 19 wherein said dielectric material is LiF.

21. The system according to claim 18 wherein said organic material is a fluorescent dye.

22. The system according to claim 13 wherein said conductive material is reflective at the wavelengths at which said fluorescence is excited and emitted.

23. The system according to claim 13 wherein said wave guide extends along said surfaces between opposite ends of said surfaces, and means for detecting said fluorescence which is emitted intermediate the ends of said wave guide.

* * * * *